United States Patent [19]

Golia

[11] 4,102,337
[45] Jul. 25, 1978

[54] BELOW KNEE ORTHOSIS

[76] Inventor: Salvatore Golia, 63-71 77 Place, Middle Village, Long Island, N.Y. 11379

[21] Appl. No.: 765,942

[22] Filed: Jan. 26, 1977

[51] Int. Cl.² ............................................. A61F 3/00
[52] U.S. Cl. .................................................. 128/80 E
[58] Field of Search ............... 128/80 F, 80 R, 80 E, 128/87 R, 83, 88, 85

[56] References Cited

U.S. PATENT DOCUMENTS

| 2,107,095 | 2/1938 | Wagner | 128/80 F |
| 2,558,986 | 7/1951 | Seelert | 128/80 F |
| 3,805,773 | 4/1974 | Sichau | 128/80 E |
| 3,999,540 | 12/1976 | Freeman | 128/80 R |

Primary Examiner—John D. Yasko
Attorney, Agent, or Firm—Steinberg & Blake

[57] ABSTRACT

A device for below knee orthosis is in the form of brace having a foot plate provided with an upper surface adapted to be situated beneath a foot. Below this upper surface the foot plate is formed just to the rear of the arch region, but forwardly of the rear end of the heel region, with a transverse slot extending inwardly from at least one side of the foot plate, this slot being adapted to receive the lower horizontal leg of a substantially L-shaped lower bar member which has an upright leg extending upwardly from the lower horizontal leg thereof. To the top end of the upright leg is pivotally connected an upper upright bar portion for a given degree of turning movement with respect to the upright leg of the lower bar portion, and this upper bar portion carries at its upper end region a strap which is adapted to encircle a leg. An ankle strap is operatively connected with the foot plate to the rear of the slot thereof for securing the structure to the ankle, while the upper strap secures the upright bar structure to the leg. All of the above structure forms a separate unit capable of being removably received in a shoe, so that different shoes may be used with the same unit.

9 Claims, 12 Drawing Figures

U.S. Patent  July 25, 1978  Sheet 1 of 3  4,102,337
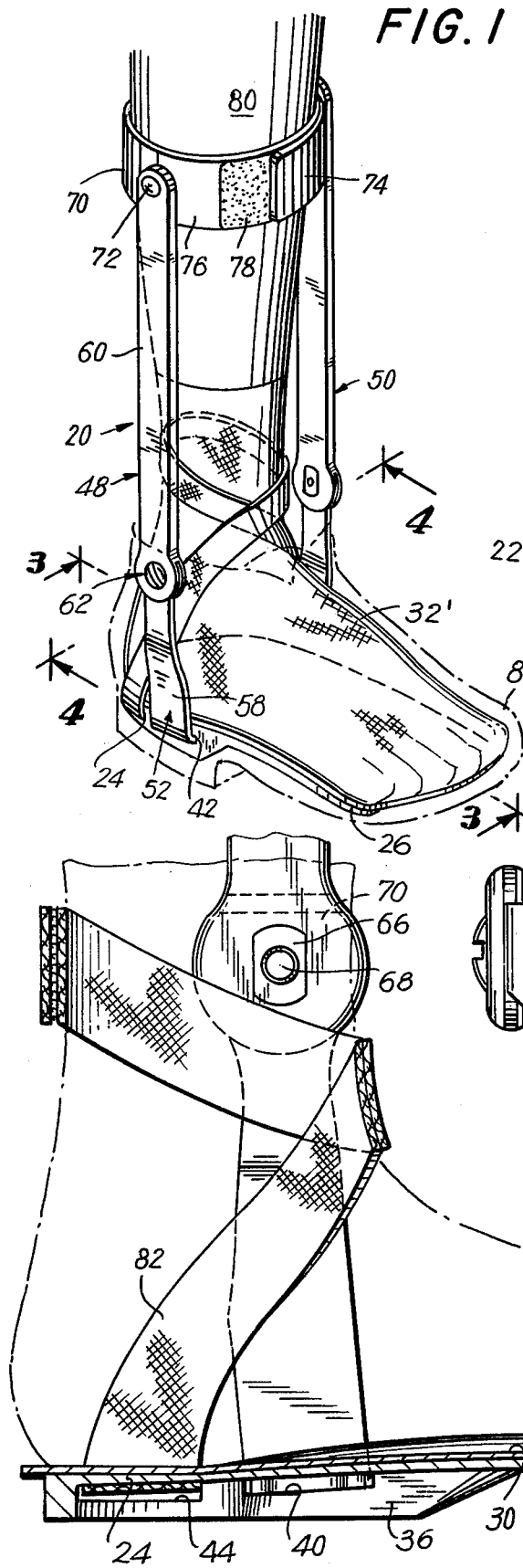
FIG. 1
FIG. 3
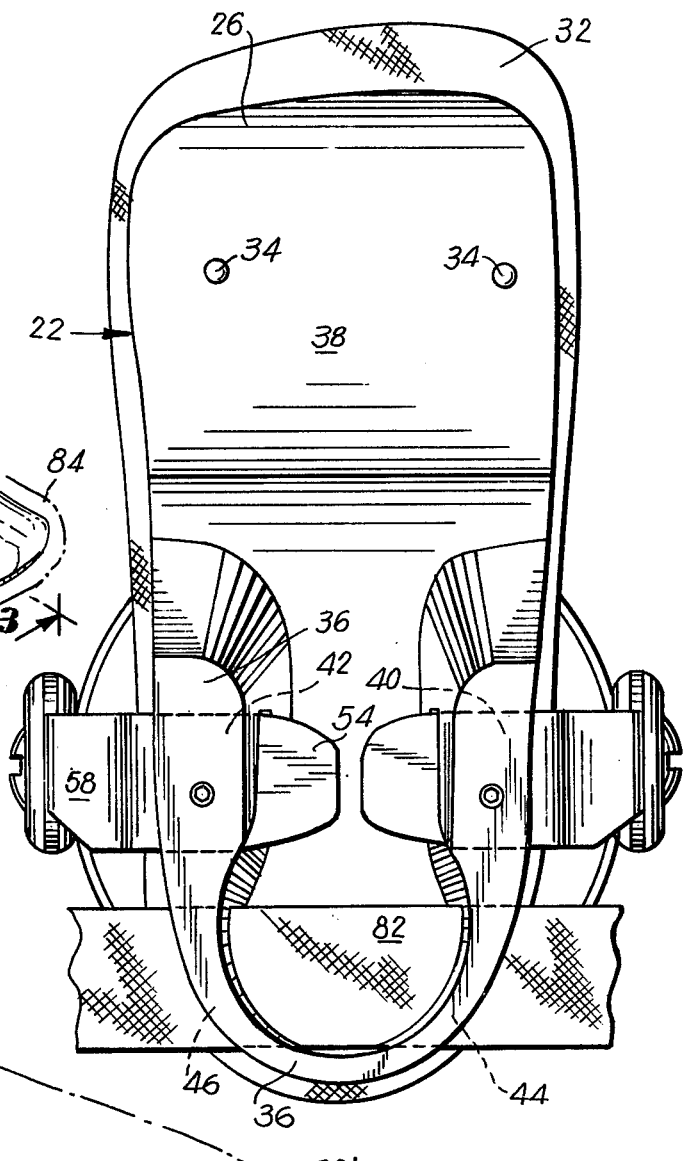
FIG. 2

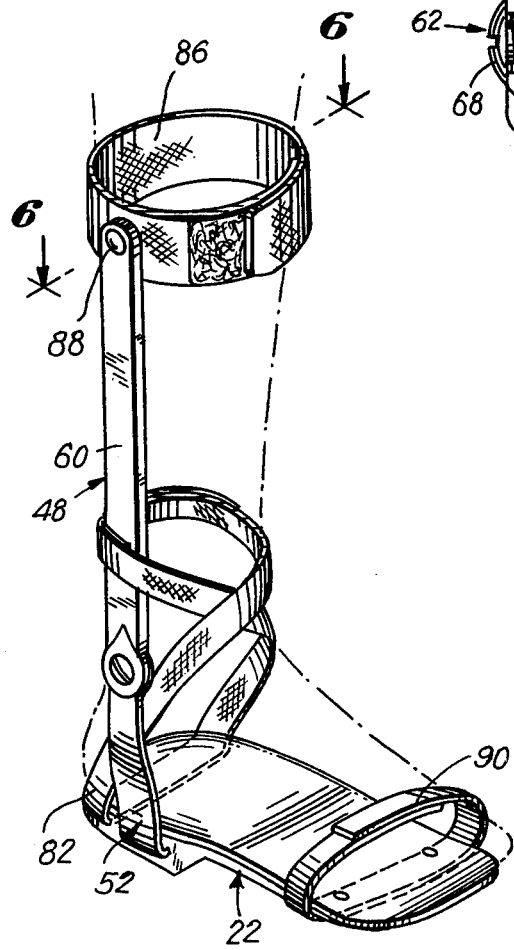
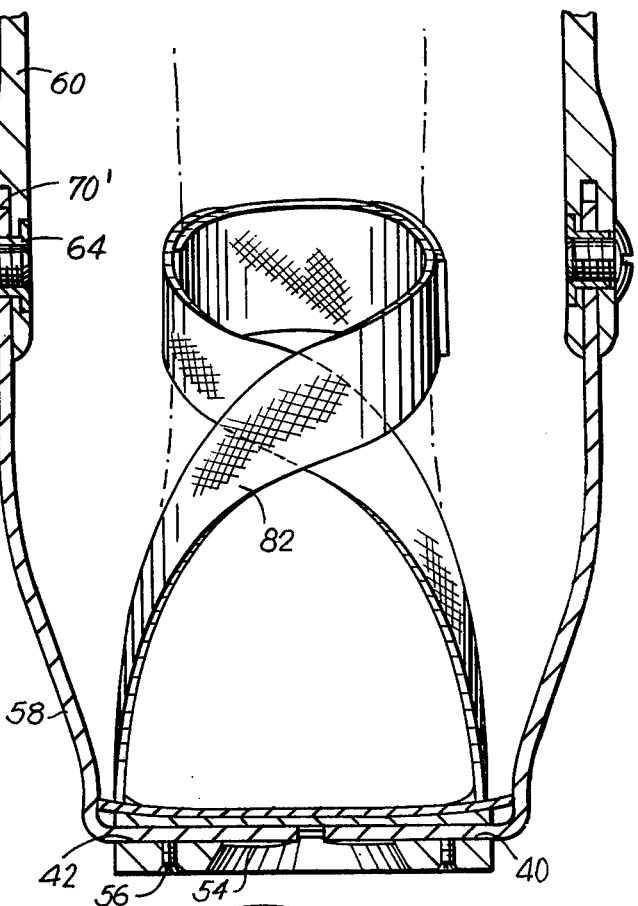
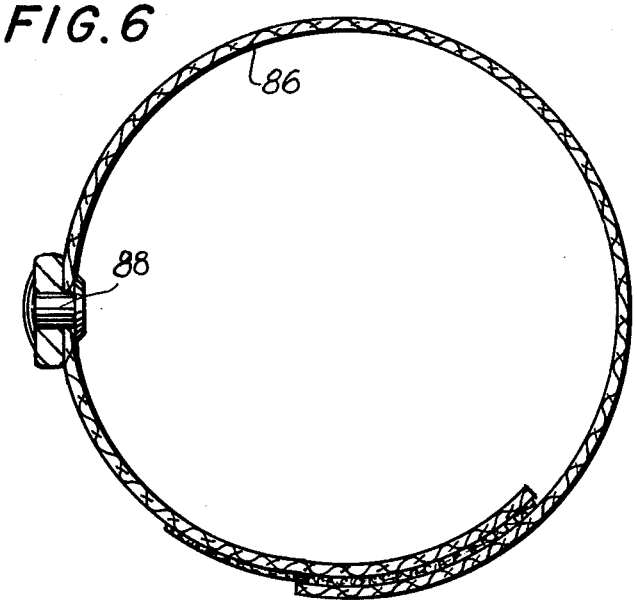
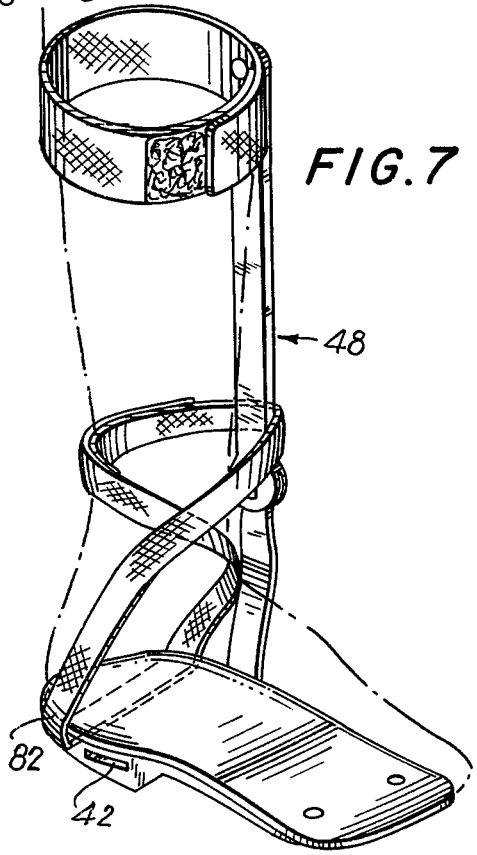

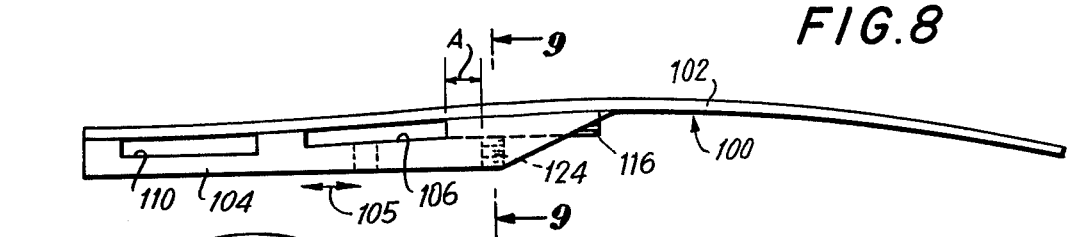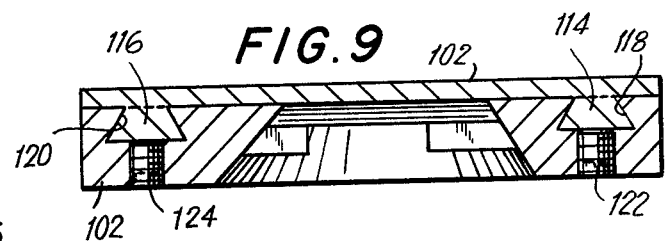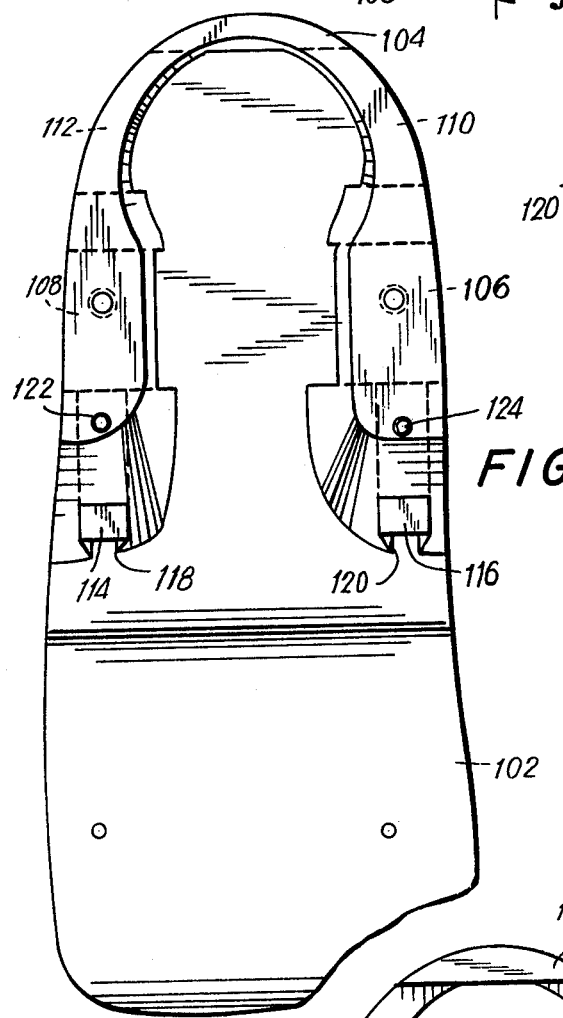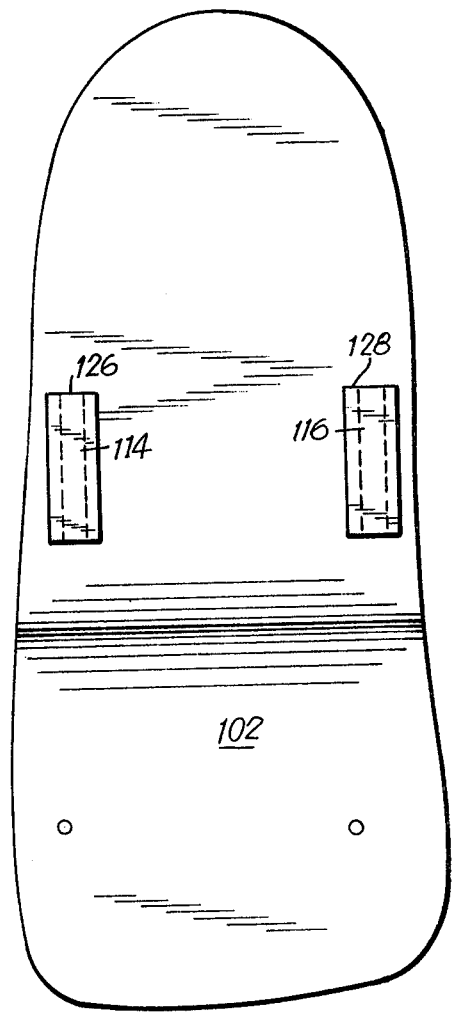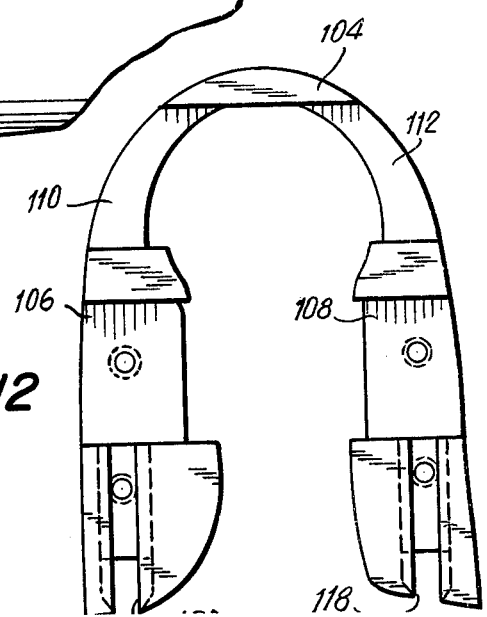

BELOW KNEE ORTHOSIS

BACKGROUND OF THE INVENTION

The present invention relates to below knee orthosis.

In particular, the present invention relates to braces intended to be used for purposes such as correction of footdrop, calcaneous conditions, or for stretching tight heel cords, or other corrective measures in connection with the ankle, for example.

Although devices of the above general type are already known, the known devices suffer from many drawbacks. Thus the known devices are heavy and cumbersome as well as expensive and complicated. In general, these known devices are built into and form part of a shoe, for example, so that in effect it is essential to provide specially made shoes which incorporate the known devices for providing the below knee orthosis. Thus, one of the great drawbacks of conventional devices of the above type resides in the fact that they must be made to order for a given individual, which requirement of course is one of the reasons for the high cost of such known devices.

While these known devices suffer from the above drawbacks when worn during the day, they are particularly undesirable when worn at night while the individual wearing the device sleeps.

SUMMARY OF THE INVENTION

It is accordingly a primary object of the present invention to provide a device which will avoid the above drawbacks.

In particular, it is an object of the present invention to provide a device of the above type which is made of separate components which can be joined together in a simple effective manner to be adapted to a given individual, thus enabling the separate components to be separately manufactured with different components being joined together according to the requirements of a given individual.

Furthermore it is an object of the present invention to provide a device of the above type which can be removably introduced into a shoe, so that it is not required to incorporate the device into a shoe as a permanent part thereof, thus enabling different shoes to be worn with the device of the invention, while also enabling the device of the invention to be used without a shoe during the night, so that if it is required that the device be worn while sleeping, the inconveniences involved with conventional devices are avoided.

It is furthermore an object of the present invention to provide a device of the above type which is not only simple and inexpensive but which at the same time is relatively light, so that the device of the invention can be used with far more comfort than conventional devices.

In addition it is an object of the present invention to provide a device of the above type which is adjustable to a degree far greater than has hitherto been possible, so that it is possible to approach with the device of the invention ideal corrective conditions in a manner which cannot be matched by previously known devices.

According to the invention the below knee orthosis is in the form of a brace which comprises a foot plate means having a front toe region, a rear heel region, and an intermediate arch region, this foot plate means having an upper surface adapted to be situated beneath a foot. The foot plate means is formed with at least one transverse slot situated beneath its upper surface and extending inwardly from a side of the foot plate means at a location situated at the rear of the intermediate arch region but forwardly of a rear end of the heel region of the foot plate means. An upright bar means has a lower substantially L-shaped bar portion provided with a lower substantially horizontal leg adapted to be received in this slot, and with a substantially upright leg extending upwardly from the lower leg. The upright bar means also has an upper bar portion extending upwardly from the upright leg of the lower bar portion. The upright bar means includes a pivot means interconnecting the upper bar portion at a lower end region thereof and a lower bar portion at an upper end region thereof pivotally to each other for providing a given degree of turning of the upper bar portion with respect to the lower bar portion about an axis extending transversely across the foot plate means. The upper bar portion of the upright bar means terminates in an upper end region distant from the lower bar portion. An upper strap means is connected with this upper end region of the upper bar portion for encircling a leg above the ankle so as to secure the upright bar means at the upper end region of its upper bar portion to a leg. An ankle strap means is operatively connected with the foot plate means to the rear of the slot thereof securing the foot plate means to a foot at the region of the ankle thereof. The above foot plate means, upright bar means, upper strap means, and ankle strap means form a unit separate from a shoe and capable of being removably inserted into a shoe, so that this unit can be used with different shoes.

BRIEF DESCRIPTION OF DRAWINGS

The invention is illustrated by way of example in the accompanying drawings which form part of this application and in which:

FIG. 1 is a perspective illustration of one embodiment of the invention;

FIG. 2 shows the structure of FIG. 1 in a bottom plan view at a scale larger than FIG. 1;

FIG. 3 is a longitudinal section of the structure of FIG. 1 taken along line 3—3 of FIG. 1 in the direction of the arrows and also showing the structure at a scale larger than FIG. 1;

FIG. 4 is a transverse section of the structure of FIG. 1 taken along line 4—4 of FIG. 1 in the direction of the arrows and also showing the structure at a scale which is enlarged as compared to FIG. 1;

FIG. 5 is a perspective illustration of another embodiment of the invention;

FIG. 6 is a sectional plan view taken along line 6—6 of FIG. 5 in the direction of the arrows and showing the structure at a scale larger than FIG. 5;

FIG. 7 shows the components of FIG. 5 assembled together in a manner different from FIG. 5;

FIG. 8 is a side elevation of another embodiment of a foot plate means of the invention;

FIG. 9 is a transverse section of the structure of FIG. 8 taken along line 9—9 of FIG. 8 in the direction of the arrows;

FIG. 10 is a bottom plan view of the structure of FIG. 8;

FIG. 11 shows only the upper part of the foot plate means of FIG. 8 as it appears when looking toward the bottom thereof; and FIG. 12 shows only the lower part of the foot plate means of FIG. 8 as it appears when looking downwardly at the top thereof.

DESCRIPTION OF PREFERRED EMBODIMENTS

Referring first to FIGS. 1–4, the brace 20 of the present invention which is illustrated therein includes a foot plate means 22. This foot plate means 22 has a rear heel region 24, a front toe region 26, and an intermediate arch region 28. The entire foot plate means 22 is relatively rigid and may be made of a suitable metal such as stainless steel. The foot plate means 22 has an upper surface 30 adapted to be situated beneath a foot 32 shown in phantom lines in FIG. 3. In the illustrated example, the upper surface 30 is covered with a thin layer of a sheet material 32 such as a suitable plastic which may extend slightly beyond the periphery of the foot plate means 22, as is shown most clearly in FIG. 2. This thin layer of flexible sheet material renders the foot plate means more comfortable to the foot 32'. The sheet material 32 can be fixed to the upper surface 30 of the foot plate means 22 in any suitable way, and in the illustrated example a pair of rivets 34 are provided for this purpose.

In the example of FIGS. 1–4, the foot plate means 22 has a substantially U-shaped portion 36 projecting downwardly from the lower surface 38 of the foot plate means 22 and extending along the periphery thereof at the heel region 24 and up to and along part of the intermediate arch region 28. Beneath its upper surface 30, the foot plate means 22 is formed with a transverse slot means just to the rear of the intermediate arch region 28, this transverse slot means including a pair of transverse slots 40 and 42 which are in line with each other. These transverse slots 40 and 42 extend inwardly from opposed sides of the foot plate means transversely across the latter and completely through the U-shaped portion 36. This U-shaped portion 36 is formed integrally with the remainder of the foot plate means 32. To the rear of the pair of slots 40 and 42, the foot plate means 22 is formed with an additional pair of slots 44 and 46 which also extend transversely across the foot plate means and completely through the U-shaped portion 36, as is apparent from FIGS. 2 and 3. By making the downwardly extending portion 36 of the U-shaped configuration illustrated it is possible to save a considerable amount of weight and to render the foot plate means far more comfortable to the wearer.

In the embodiment of FIGS. 1–4, the brace 20 includes a pair of upright bar means 48 and 50. The upright bar means 48 includes a lower bar portion 52 of substantially L-shaped configuration having a lower horizontal leg 54 received in the slot 42 and capable of being releasably fixed therein, if desired, by way of a set screw 56, although this set screw is not at all essential. The lower bar portion 52 has in addition to its horizontal leg 54 an upright leg 58 extending upwardly from the horizontal leg 54 at the outside of the foot plate means 22 as shown in FIGS. 1 and 4. This upright bar means 48 includes an upper substantially straight bar portion 60 which has a lower end region pivotally connected with an upper end region of the lower bar portion 52 by way of a pivot means 62. Thus it will be seen that the upright leg 58 of the lower bar portion 52 is received in a slit which is formed in the lower end region of the upper bar portion 60. The overlapping parts of the upper and lower bar portions are formed with aligned openings which receive a sleeve 64, shown most clearly in FIG. 4. This sleeve 64 is formed with an inner substantially rectangular flange portion 66 (FIG. 3) received in a correspondingly shaped opening in the lower end region of the upper bar portion 60. This sleeve 64 is formed with an internal thread for receiving the threads of a screw member 68 which thus forms with the sleeve 64 the pivot means 62. The upright leg 58 of the lower bar portion 52 terminates in an upper straight edge 70' situated at a given distance below the innermost part of the slit which receives the upper end region of the leg 58, so that in this way a given degree of turning is provided for the upper bar portion 60 with respect to the lower bar portion 52. Of course, it is possible to select for the top end of the leg 58 a different configuration according to which a greater amount of pivotal movement can be provided for the upper bar portion 60 with respect to the lower bar portion 52.

As is apparent from the drawings, the upright bar means 50 is identical with the upright bar means 48, the only difference being that the bar means 50 is oriented oppositely to the bar means 48 so that the inner surfaces of these bar means are directed toward each other while the lower legs of the lower bar portions thereof can be respectively received in the slots 40 and 42 as illustrated.

An upper strap means 70 is in the form of a flexible substantially non-stretchable sheet material such as a suitable heavy fabric fixed, as by rivets 72 to the upper end regions of the upper bar portions of the upright bar means 48 and 50, so that by way of the rivets 72 the upper strap means 70 can swivel about a horizontal axis which extends transversely across the foot plate means 22. While the strap means 70 extends continuously substantially along a semicircle between the rivets 72 to the rear thereof, forwardly of the rivets the strap means 70 has a pair of separate portions 74 and 76 capable of being overlapped with respect to each other, as shown in FIG. 1, and releasably fixed to each other as by a Velcro fastening structure 78. Thus, by way of the upper strap means 70 it is possible to secure the pair of upright bar means 48 and 50 to the leg 80 above the ankle thereof, with the foot 32 of the leg 80 resting on the foot plate means 22 as described above.

The above-described structure of the invention is completed by an ankle strap means 82 also in the form of a flexible but substantially non-stretchable strip of sheet material such as a heavy fabric. This ankle strap means 82 is operatively connected with the foot plate means 22 by extending through the slots 44 and 46 formed in the U-shaped portion 36 of the foot plate means. The central region of the ankle strap means 82 extends through these slots 44 and 46 and across the lower surface 38 of the foot plate means 22, as indicated in FIG. 2. From the slots 44 and 46 it is possible to extend the ankle strap means 82 forwardly up over the instep, where the strap 82 has portions which also overlap each other and then extend to the rear of and partly around the ankle where the free end portions of the strap 82 are releasably fixed to each other as by a suitable Velcro fastener as illustrated.

A number of advantages are achieved by the above-described structure of the embodiment of FIGS. 1–4. Thus, by making the foot plate means 22 separate from the pair of upright bar means, it is possible to join different sets of upright bar means of different sizes with different foot plate means which are also of different sizes, and it is a simple matter to slip the horizontal legs of the lower bar portions into the pair of opposed slots 40 and 42 with the set screws 56 if they are present being used to releasably hold the upright bar means in predetermined positions with respect to the foot plate means. Also it is to be noted that different degrees of turning can be provided between the upper and lower bar portions of each upright bar means as set forth above, depending upon the particular below knee orthosis which is required. Because of the flexibility of the upper strap means 70 it is possible to join the latter to the upper end regions of the upper bars of the pair of upright bar means 48 and 50 before the latter are joined with the foot plate means. Of course the ankle strap means 82 is slipped through the slots 44 and 46 to provide the above-described construction.

With the above structure it is a simple matter for an individual to place his foot on the foot plate means between the pair of upright bar means 48 and 50 and then to fasten the upper strap means 70 to the leg above the ankle and the lower strap means 82 around the ankle in the manner described above and shown in the drawings, so as to complete the placing of the brace of the invention on the individual.

A particularly important feature of the present invention resides in the fact that this brace means of the invention forms no part of a shoe. However because of its light weight and unencumbered construction, it is a simple matter for this brace of the invention to be slipped into a shoe such as the shoe 84 which is shown in phantom lines in FIG. 1. If desired the brace structure can first be introduced into the shoe 84 and then the foot of the individual can be placed in the brace structure, or the brace structure preferably is placed first on the foot and then the foot with the brace structure thereon is slipped into the shoe 84. In the event, by reason of this feature of the invention it is possible to remove the brace of the invention, the components of which form a unit separate from the shoe 84, from the shoe 84 whenever desired, so that it is possible to replace the shoe 84 with another shoe while utilizing the same brace structure. Furthermore, since the brace unit of the invention does not form part of a shoe, if it is required for an individual to wear the brace structure while sleeping, this can easily be carried out in a very comfortable way without the necessity of wearing the shoe while sleeping.

The embodiment of the invention which is illustrated in FIG. 5 includes a foot plate means 22 identical with that described above. Also this embodiment includes an upright bar means 48 identical with that described above. However, in this embodiment only a single upright bar means is provided, and it will be noted that in FIG. 5 this upright bar means 48 is connected to the foot plate means 22 at the outer side thereof. The embodiment of FIG. 5 includes an upper strap means 86 which may be identical with the strap means 70 except that the strap means 86 is connected only to the upper end region of the upright bar means 48 in the manner illustrated in FIG. 5. In this particular example the rivet 88 used to fix the upper strap means 86 to the upright bar means 48 enables the strap means 88 to swivel through 180° in either direction around the axis of the rivet 88 which extends transversely across the foot plate means 22.

This embodiment of the invention is utilized when it is desired to provide a force urging the ankle toward the outer side of the foot, and for this purpose the ankle strap means 82 of FIG. 5, which is identical with the ankle strap means of FIGS. 1-4, extends around the outside of the upper portion 60 of the upright bar means 48 in the manner illustrated in FIG. 5.

Thus, the construction shown in FIGS. 5 and 6 can be used for the situation where such a one-sided orthosis is required, and this structure also can be easily slipped into and out of any one of a number of different shoes.

FIG. 5 shows a front toe strap means 90 which can be passed around the toe portion of the foot plate means 22 and held together above the toe region of the foot through a suitable fastener such as a Velcro fastener. This toe strap means 90 is used when the brace of the invention is utilized during sleeping without a shoe.

According to a further feature of the invention it is possible to provide for the components of FIGS. 5 and 6 a different assembly as illustrated in FIG. 7, when it is desired to urge the ankle toward the inner side in a direction opposite to that shown for the arrangement of FIG. 5. Thus in FIG. 7 the upright bar means 48 has the lower horizontal leg of its lower bar portion 52 situated in the slot 40 rather than the slot 42, and the ankle strap means 82 in this case is also passed around the outside of the upright bar means 48 in the manner illustrated in FIG. 7.

When converting the structure of FIG. 5 to the arrangement illustrated in FIG. 7, the upper strap means 86 is turned about the pivot 88 through 180° so that the free ends of the strap means 86 will still be situated at the front of the leg to be conveniently fastened at the front of the leg in the manner which is apparent from FIG. 7.

Thus the components of the invention illustrated in FIGS. 5-7 can easily be assembled together in a highly convenient manner to provide either the arrangement of FIG. 5 or the arrangement of FIG. 7 so as to achieve different results with the same structure.

Moreover, it will be noted that except for the upper strap means 86 the components of FIG. 5 are identical with those of FIGS. 1-4. Thus it is a simple matter to attach the strap means 86 to one of the bar means of the embodiment of FIGS. 1-4 in order to achieve the structure of FIGS. 5-7.

FIGS. 8-12 illustrate a foot plate means 100 which may be used with any of the above embodiments. This foot plate means 100 includes an upper foot plate member 102 and a lower foot plate member 104, the latter being the substantially U-shaped member 36 which in the embodiment of FIGS. 8-12 is made separate from the plate 102 of the foot plate means 100. Thus in this case the lower member 104 is formed at its upper surface with transverse notches 106 and 108 to define with the lower surface of the plate 102 the equivalent of the slots 42 and 40, respectively, while this member 104 is formed with rear notches 110 and 112 to define with the lower surface of the plate 102 the equivalent of the rear slots 46 and 44.

The embodiment of the foot plate means shown in FIGS. 8-12 has the capability of adjusting the member 104 with respect to the member 102 forwardly and rearwardly, as indicated by the double-headed arrow 115 in FIG. 8, so that in this way it is possible to precisely situate the several notches, and in particular the notches 106 and 108, thus enabling the longitudinal location of the upright bar means to be precisely determined in a manner which is ideal for a particular individual.

For this purpose the structure includes a pair of elongated members 114 and 116 of substantially dovetail or trapezoidal cross section which may be integral with the plate 102 or which may be fixed thereto in any suitable way at the locations apparent from FIG. 11. Thus these members 114 and 116 extend downwardly from the lower surface of the plate 102.

The member 104 is formed forwardly of the front notches 106 and 108 thereof with longitudinal slots 118 and 120 which respectively receive the members 114 and 116 and which are of a cross section matching that of the members 114 and 116. In this way dovetail guides are provided between the member 104 and plate 102 for guiding the member 104 in the manner indicated by the arrow 115 so that in this way it is possible to adjust the location of the member 104 with respect to the plate 102 and thus adjust the location of the notches 106 and 108 for the purpose described above. The member 104 is formed at its front end region with a pair of threaded bores receiving set screws 122 and 124 which can releasably hold the member 104 in an adjusted position.

It is to be noted that the guide members 114 and 116 have rear ends 126 and 128 situated forwardly of the notches 106 and 108 by the distance A illustrated in FIG. 8, when the member 104 is situated substantially at its rearmost position with respect to the plate 102, so that it is possible to adjust the member 104 forwardly through this distance A before the guide members 114 and 116 will engage the horizontal leg of the lower substantially L-shaped bar portion of one or both bar means which are to be used with the foot plate means 100 in a manner described above.

Thus, by utilizing the foot plate means 100 of FIGS. 8–12 with either one or both of the bar means and strap means as described above in connection with FIGS. 1–7, it is possible to obtain an extremely precise brace structure while still retaining all of the advantages of lightness of weight and convenience and comfort in use of the structure.

What is claimed is:

1. A brace comprising foot plate means having a front toe region, a rear heel region, and an intermediate arch region, said foot plate means having an upper surface adapted to be situated beneath a foot, and said foot plate means being formed with at least one transverse slot situated beneath said upper surface and extending inwardly from a side of said foot plate means at a location situated at the rear of said intermediate arch region but forwardly of a rear end of said heel region of said foot plate means, upright bar means having a lower substantially L-shaped bar portion provided with a lower substantially horizontal leg adapted to be received in said slot and with a substantially upright leg extending upwardly from said lower leg, said upright bar means also having an upper bar portion extending upwardly from said upright leg of said lower bar portion, said upright bar means including a pivot means interconnecting said upper bar portion at a lower end region thereof and said lower bar portion at an upper end region thereof pivotally to each other for providing a given degree of turning of said upper bar portion with respect to said lower bar portion about an axis extending transversely across said foot plate means, said upper bar portion of said upright bar means terminating in an upper end region distant from said lower bar portion, upper strap means connected with said upper end region of said upper bar portion for encircling a leg above the ankle thereof for securing said upright bar means at said upper end region of said upper bar portion thereof to a leg, and ankle strap means operatively connected with said foot plate means to the rear of said slot for securing said foot plate means to a foot at the region of an ankle thereof, said foot plate means, upright bar means, upper strap means, and ankle strap means forming a unit of separate from a shoe and capable of being removably inserted into a shoe, so that said unit can be used with different shoes, said foot plate means being formed to the rear of said slot beneath said upper surface of said foot plate means with an additional slot extending transversely of said foot plate means for receiving a part of said ankle strap means.

2. A brace comprising foot plate means having a front toe region, a rear heel region, and an intermediate arch region, said foot plate means having an upper surface adapted to be situated beneath a foot, and said foot plate means being formed with at least one transverse slot situated beneath said upper surface and extending inwardly from a side of said foot plate means at a location situated at the rear of said intermediate arch region but forwardly of a rear end of said heel region of said foot plate means, upright bar means having a lower substantially L-shaped bar portion provided with a lower substantially horizontal leg adapted to be received in said slot and with a substantially upright leg extending upwardly from said lower leg, said upright bar means also having an upper bar portion extending upwardly from said upright leg of said lower bar portion, said upright bar means including a pivot means interconnecting said upper bar portion at a lower end region thereof and said lower bar portion at an upper end region thereof pivotally to each other for providing a given degree of turning of said upper bar portion with respect to said lower bar portion about an axis extending transversely across said foot plate means, said upper bar portion of said upright bar means terminating in an upper end region distant from said lower bar portion, upper strap means connected with said upper end region of said upper bar portion for encircling a leg above the ankle thereof for securing said upright bar means at said upper end region of said upper bar portion thereof to a leg, and ankle strap means operatively connected with said foot plate means to the rear of said slot for securing said foot plate means to a foot at the region of an ankle thereof, said foot plate means, upright bar means, and ankle strap means forming a unit separate from a shoe and capable of being removably inserted into a shoe, so that said unit can be used with different shoes, said foot plate means being formed with a transverse slot means situated beneath said upper surface with said slot forming part of said transverse slot means, said transverse slot means including a second slot extending inwardly from a side of said foot plate means opposite from the side from which said first-mentioned slot extends inwardly, and said lower leg of said lower portion of said upright bar means being adapted to be selectively received in either one of said slots.

3. The combination of claim 2 and wherein said upper strap means is pivotally connected to said upper end region of said upper bar portion for turning movement with respect thereto about an axis extending transversely across said foot plate means, so that said strap means can be oriented properly depending upon which of said slots receives said lower leg of said lower bar portion of said upright bar means.

4. A brace comprising foot plate means having a front toe region, a rear heel region, and an intermediate arch region, said foot plate means having an upper surface adapted to be situated beneath a foot, and said foot plate means being formed with at least one transverse slot situated beneath said upper surface and extending inwardly from a side of said foot plate means at a location situated at the rear of said intermediate arch region but forwardly of a rear end of said heel region of said foot plate means, upright bar means having a lower substantially L-shaped bar portion provided with a lower substantially horizontal leg adapted to be received in said slot and with a substantially upright leg extending upwardly from said lower leg, said upright bar means also having an upper bar portion extending upwardly from said upright leg of said lower bar portion, said upright bar means including a pivot means interconnecting said upper bar portion at a lower end region thereof and said lower bar portion at an upper end region thereof pivotally to each other for providing a given degree of turning of said upper bar portion with respect to said lower bar portion about an axis extending transversely across said foot plate means, said upper bar portion of said upright bar means terminating in an upper end region distant from said lower bar portion, upper strap means connected with said upper end region of said upper bar portion for encircling a leg above the ankle thereof for securing said upright bar means at said upper end region of said upper bar portion thereof to a leg, and ankle strap means operatively connected with said foot plate means to the rear of said slot for securing said foot plate means to a foot at the region of an ankle thereof, said foot plate means, upright bar means, upper strap means, and ankle strap means forming a unit separate from a shoe and capable of being removably inserted into a shoe, so that said unit can be used with different shoes, said foot plate means being formed with a transverse slot means of which said slot forms a part, said transverse slot means including a second slot extending inwardly from said foot plate means at a side thereof opposite from the side from which said first-mentioned slot extends inwardly, and a pair of said upright bar means respectively having lower bar portions respectively provided with said horizontal legs which are respectively received in said slots, said pair of upright bar means respectively having upper bar portions connected by a pair of said pivot means to said lower bar portions and respectively terminating in upper end regions to which said upper strap means is connected.

5. The combination of claim 4 and wherein said foot plate means is formed to the rear of said transverse slot means with a further slot means extending transversely across said foot plate means beneath said upper surface thereof for receiving a part of said ankle strap means.

6. A brace comprising foot plate means having a front toe region, a rear heel region, and an intermediate arch region, said foot plate means having an upper surface adapted to be situated beneath a foot, and said foot plate means being formed with at least one transverse slot situated beneath said upper surface and extending inwardly from a side of said foot plate means at a location situated at the rear of said intermediate arch region but forwardly of a rear end of said heel region of said foot plate means, upright bar means having a lower substantially L-shaped bar portion provided with a lower substantially horizontal leg adapted to be received in said slot and with a substantially upright leg extending upwardly from said lower leg, said upright bar means also having an upper bar portion extending upwardly from said upright leg of said lower bar portion, said upright bar means including a pivot means interconnecting said upper bar portion at a lower end region thereof and said lower bar portion at an upper end region thereof pivotally to each other for providing a given degree of turning of said upper bar portion with respect to said lower bar portion about an axis extending transversely across said foot plate means, said upper bar portion of said upright bar means terminating in an upper end region distant from said lower bar portion, upper strap means connected with said upper end region of said upper bar portion for encircling a leg above the ankle thereof for securing said upright bar means at said upper end region of said upper bar portion thereof to a leg, and ankle strap means operatively connected with said foot plate means to the rear of said slot for securing said foot plate means to a foot at the region of an ankle thereof, said foot plate means, upright bar means, upper strap means, and ankle strap means forming a unit separate from a shoe and capable of being removably inserted into a shoe, so that said unit can be used with different shoes, said foot plate means being relatively thin and including along a peripheral part of said heel region a substantially U-shaped projection extending downwardly from a lower surface of said foot plate means and formed with said slot, said substantially U-shaped portion being formed with a second slot in line with said first-mentioned slot and extending inwardly from a side of said foot plate means opposite from the side from which said first-mentioned slot extends, so that a pair of said upright bar means can be received in said slots, respectively or so that a single upright bar means may be interchangeably received in said slots.

7. A brace comprising foot plate means having a front toe region, a rear heel region, and an intermediate arch region, said foot plate means having an upper surface adapted to be situated beneath a foot, and said foot plate means being formed with at least one transverse slot situated beneath said upper surface and extending inwardly from a side of said foot plate means at a location situated at the rear of said intermediate arch region but forwardly of a rear end of said heel region of said foot plate means, upright bar means having a lower substantially L-shaped bar portion provided with a lower substantially horizontal leg adapted to be received in said slot and with a substantially upright leg extending upwardly from said lower leg, said upright bar means also having an upper bar portion extending upwardly from said upright leg of said lower bar portion, said upright bar means including a pivot means interconnecting said upper bar portion at a lower end region thereof and said lower bar portion at an upper end region thereof pivotally to each other for providing a given degree of turning of said upper bar portion with respect to said lower bar portion about an axis extending transversely across said foot plate means, said upper bar portion of said upright bar means terminating in an upper end region distant from said lower bar portion, upper straip means connected with said upper end region of said upper bar portion for encircling a leg above the ankle thereof for securing said upright bar means at said upper end region of said upper bar portion thereof to a leg, and ankle strap means operatively connected with said foot plate means to the rear of said slot for securing said foot plate means to a foot at the region of an ankle thereof, said foot plate means, upright bar means, upper strap means, and ankle strap means forming a unit separate from a shoe and capable of being removably inserted into a shoe, so that said unit can be used with different shoes, said foot plates means being relatively thin and including along a peripheral part of said heel region a substantially U-shaped projection extending downwardly from a lower surface of said foot plate means and formed with said slot, said substantially U-shaped portion being formed to the rear of said transverse slot with additional transverse slots for receiving part of said ankle strap means.

8. A brace comprising foot plate means having a front toe region, a rear heel region, and an intermediate arch region, said foot plate means having an upper surface adapted to be situated beneath a foot, and said foot plate means being formed with at least one transverse slot situated beneath said upper surface and extending inwardly from a side of said foot plate means at a location situated at the rear of said intermediate arch region but forwardly of a rear end of said heel region of said foot plate means, upright bar means having a lower substantially L-shaped bar portion provided with a lower substantially horizontal leg adapted to be received in said slot and with a substantially upright leg extending upwardly from said lower leg, said upright bar means also having an upper bar portion extending upwardly from said upright leg of said lower bar portion, said upright bar means including a pivot means interconnecting said upper bar portion at a lower end region thereof and said lower bar portion at an upper end region thereof pivotally to each other for providing a given degree of turning of said upper bar portion with respect to said lower bar portion about an axis extending transversely across said foot plate means, said upper bar portion of said upright bar means terminating in an upper end region distant from said lower bar portion, upper strap means connected with said upper end region of said upper bar portion for encircling a leg above the ankle thereof for securing said upright bar means at said upper end region of said upper bar portion thereof to a leg, and ankle strap means operatively connected with said foot plate means to the rear of said slot for securing said foot plate means to a foot at the region of an ankle thereof, said foot plate means, upright bar means, upper strap means, and ankle strap means forming a unit separate from a shoe and capable of being removably inserted into a shoe, so that said unit can be used with different shoes, said foot plate means being relatively thin and including along a peripheral part of said heel region a substantially U-shaped projection extending downwardly from a lower surface of said foot plate means and formed with said slot, said substantially U-shaped portion being separate from the remainder of said foot plate means, and adjusting means interconnecting said substantially U-shaped portion of said foot plate means with the remainder thereof for adjusting the location of said U-shaped portion longitudinally along said foot plate means at a selected location between said heel and toe regions thereof, to adjust the position of said slot.

9. The combination of claim 6 and wherein said substantially U-shaped portion is integral with the remainder of said foot plate means.

* * * * *